United States Patent [19]

Buffet

[11] Patent Number: 4,522,208
[45] Date of Patent: Jun. 11, 1985

[54] METHOD FOR DETERMINING PARAMETER VALUES OF AN IMPLANTED PROGRAMMABLE PACEMAKER

[75] Inventor: Jacques Buffet, Le Raincy, France

[73] Assignee: Cardiofrance Compagnie Francaise D'Electrocardiologie, Le Grand, France

[21] Appl. No.: 583,578

[22] Filed: Feb. 24, 1984

Related U.S. Application Data

[63] Continuation-in-part of Ser. No. 254,860, Apr. 16, 1981, abandoned.

[51] Int. Cl.³ ............................................. A61N 1/36
[52] U.S. Cl. .......................... 128/419 PT; 128/419 PG
[58] Field of Search .................... 128/419 PT, 419 PG

[56] References Cited

U.S. PATENT DOCUMENTS

| | | | |
|---|---|---|---|
| 3,837,348 | 9/1974 | Thaler | 128/419 PT |
| 4,124,031 | 11/1978 | Mensink et al. | 128/419 PT |
| 4,211,235 | 7/1980 | Keller, Jr. et al. | 128/419 PG |
| 4,232,679 | 11/1980 | Schulman | 128/419 PG |
| 4,304,238 | 12/1981 | Fischer | 128/419 PG |
| 4,323,074 | 4/1982 | Nelms | 128/419 PG |
| 4,428,378 | 1/1984 | Anderson et al. | 128/419 PG |

*Primary Examiner*—William E. Kamm

[57] ABSTRACT

In order to determine parameter values of an implanted programmable pacemaker, each parameter value is assigned a time ΔT which is a fraction of the pacing period T in the magnetic mode. In a pair of successive pacing intervals with the combined duration of 2T, one interval is shortened and the other lengthened by the amount ΔT. With the pacemaker in the magnetic mode, the parameter value is identified by observing the position of the middle pulse in the double interval 2T.

3 Claims, 5 Drawing Figures

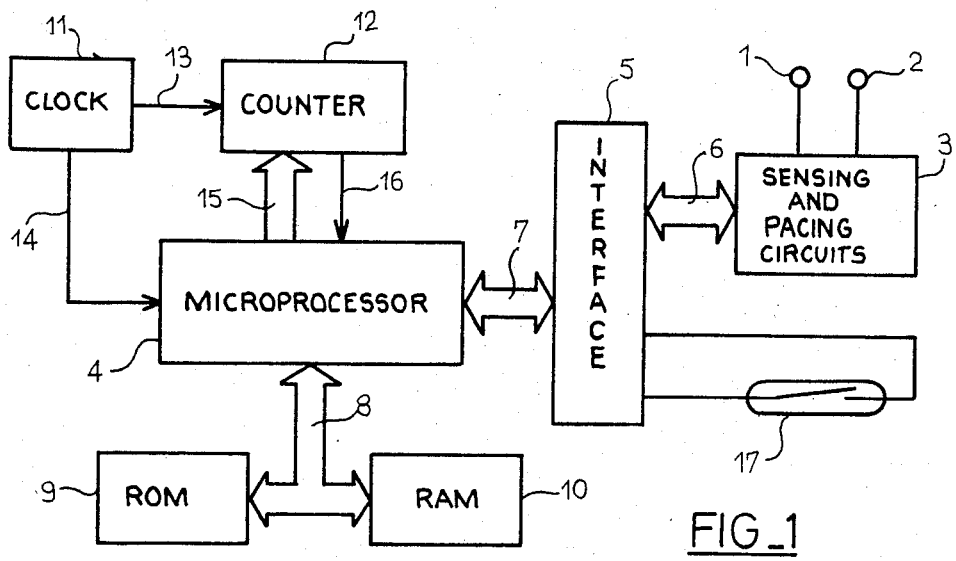
FIG_1
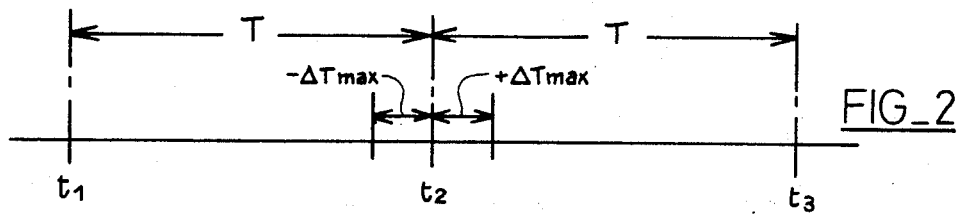
FIG_2
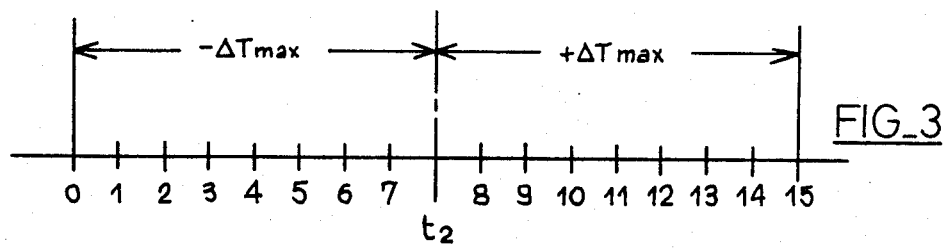
FIG_3
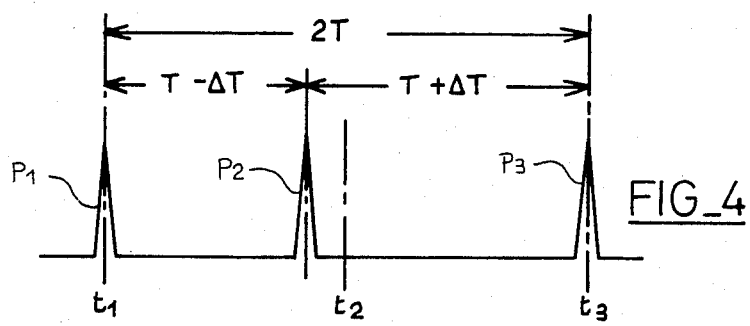
FIG_4

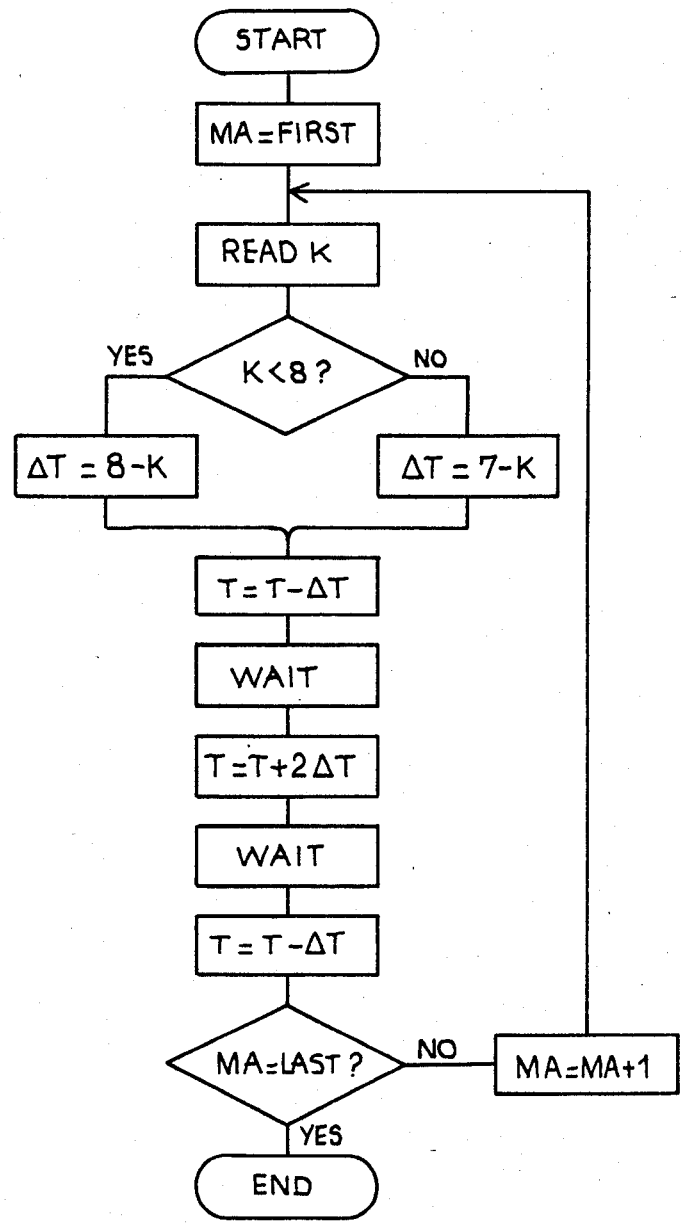
FIG_5

METHOD FOR DETERMINING PARAMETER VALUES OF AN IMPLANTED PROGRAMMABLE PACEMAKER

This is a continuation-in-part of Ser. No. 254,860, now abandoned.

BACKGROUND OF THE INVENTION

1. Field of the Invention

This invention relates to implantable cardiac pacemakers of the kind which are externally programmable for changing certain operating parameters. More particularly, the invention relates to a method of externally determining the actual parameter values which have been programmed into an implanted pacemaker.

2. The Prior Art

Programmable pacemakers have provisions for the external programming of various parameters, such as stimulation pulse rate, escape interval, refractory period, pulse width, pulse amplitude, and sensitivity. Also programmable is the mode of operation, such as demand, synchronous and asynchronous.

Communication between the external programmer and the pacemaker may be by means of radio waves, ultrasound, by magnetic fields, or by other means. Usually, the pacemaker is provided with a reed switch which may be closed by the application of an external magnet, thereby causing the pacemaker to be switched into asynchronous mode. A programmable pacemaker of this kind is described in U.S. Pat. No. 4,124,031. According to this patent, the magent is also used for programming, in that it is alternately removed from and applied to the patient in predetermined sequences of varying durations. Although this method of programming has the advantage of not requiring any special programming apparatus, it has the disadvantage that the pacemaker may be inadvertently programmed incorrectly if a mistake is made in the sequence of applications and removals of the magnet. It is therefore desirable, in a programmable pacemaker, to have the possibility of checking the actual programmed settings. It should be noted that apart from the stimulation pulse rate, most of the programmable parameters mentioned above are not observable on ECG equipment.

A circuit for determining the parameter control states of an implanted pacemaker is described in U.S. Pat. No. 4,190,055. According to this patent, the contents of a binary register containing the control inputs to the parameter controlling circuitry of the pacemaker are converted into serial form by means of a parallel to serial converter. The appearance of one logic state in the serial output causes a delay to be added between simulating pulses, while the appearance of the other logic state does not affect the pulse rate, so that for instance a logic one will appear as a longer interval between pulses than the intervals representing a logic zero.

SUMMARY OF THE INVENTION

It is the main object of the present invention to provide a method by means of which the values of the programmable parameters of an implanted pacemaker may be easily and accurately determined externally, even when there are a large number of programmable parameters having a large range of possible settings.

Another object of the invention is to provide a method which ascertains an accurate read-out of parameter values regardless of the state of the pacemaker battery.

BRIEF DESCRIPTION OF THE DRAWINGS

FIG. 1 is a block diagram of a pacemaker to which the present invention is applicable.

FIG. 2 is a diagram illustrating the principle of the invention.

FIG. 3 is a enlarged portion of FIG. 2.

FIG. 4 is a diagram illustrating the relative positions of pacing pulses.

FIG. 5 is a flow chart of a program by means of which the present method may be performed with the microprocessor-controlled pacemaker according to FIG. 1.

DETAILED DESCRIPTION OF THE INVENTION

In the block diagram of FIG. 1, only the circuits necessary to explain this invention are shown. The sensing and pacing electrodes 1 and 2 of the pacemaker are connected to sensing and pacing circuits 3 which communicate with a microprocessor 4 via an interface 5. A bus 6 is shown interconnecting the circuits 3 and the interface 5, and another bus 7 connects the interface with the microprocessor 4. A bus 8 connects the microprocessor with a program memory (ROM) 9 and a random acces memory 10. The programmed values of all the programmable parameters are stored in the RAM 10. The pacing period is determined by a clock 11 and a counter 12. The clock 11 is connected to the counter 12 by means of a line 13 and also has a connection 14 to the microprocessor. The counter is pre-settable by the microprocessor via lines 15 and has a connection 16 to the microprocessor on which a signal appears when the preset number of clock pulses have been counted. If, as an example, the clock pulse frequency on the line 13 is 100 Hz and the pacing period is set at 800 ms, corresponding to a pacing rate of 75 pulses per minute, the microprocessor will set the counter 12 to 80. After 80 clock pulses on the line 13, i.e. after 800 ms, the counter will produce an output signal on line 16, whereupon the microprocessor triggers a pacing pulse and again sets the counter 12 to 80.

Connected to the interface 5 is a reed switch 17 which, when caused to close by means of an external magnet, will cause the pacemaker to be switched into asynchronous mode with a predetermined pacing rate. Other parameters, such as pulse width and amplitude, may also by set to preselected values by the closing of the reed switch 17. The previous operating mode and parameter values are retained in the memory 10, so that upon removal of the magnet the pacemaker will return to its previous mode of operation and parameter settings, unless these have been reprogrammed while the pacemaker was in the magnetic mode.

Since the programming as such does not form any part of the present invention, no programming means have been shown in the drawings. If the communication between the pacemaker and the external programmer is by means of for instance radio waves or ultrasound, there would be a receiving and transmitting circuit connected to the interface 5. In the present example, it is assumed that communication is by means of electrical signals across electrodes applied to the patient's body, such electrodes being for instance in the form of bracelets attached to the patient's wrists. The programmer would be adapted to sense the pacing pulses, synchronise itself therewith the transmit information in the periods between pacing pulses. The electrical signals representing this programming information would be picked up by the sensing electrode of the pacemaker and transferred to the microprocessor 4 via the interface 5.

By transmitting a special code from the programmer, the microprocessor may be made to read out the parameter values from the RAM 10. According to this invention, the parameter values are transmitted from the pacemaker to the programming unit by means of a code which consists in shortening and lengthening the pacing periods in a special way which will be described in the following.

FIG. 2 is a time diagram of two consecutive pacing periods, each of the duration T. The position of the pacing pulse starting the first pacing period is indicated at t1, t2 indicates the position of the pulse ending the first and starting the second period, and t3 marks the position of the pulse ending the second period. The period T is the pacing period in the aforementioned magnetic or asynchronous mode. If, as an example, the pacing rate in the magnetic mode is 100 pulses per minute, the period T will be 600 ms, corresponding to 60 clock pulses to the counter 12, assuming a clock pulse frequency of 100 Hz. When the value of a parameter is read out, the center pulse is displaced from the position t2 by an amount $\Delta T$ within the range indicated in FIG. 2 by $-\Delta T max$ and $+\Delta T max$ to the left and right, respectively, of the center position t2. The value of $\Delta T$ is related to the value of the parameter, so that the parameter value can be determined by observing the position of the center pulse. With reference to FIG. 3, assuming a maximum of sixteen possible values for any parameter, corresponding to four bits of memory in the RAM 10, the first eight values correspond to $\Delta T$ displacements numbered 0 to 7 within the range $-\Delta T max$ to the left of the center position t2, and the remaining eight values correspond to $\Delta T$ displacements numbered 8 to 15 within the range $+\Delta T max$ to the right of the center position t2. If the parameter value is in the range from 0 to 7, according to FIG. 3, the corresponding time $\Delta T$ is subtracted from the first pacing period T and added to the second pacing period T. If the parameter value is within the range 8 to 15, the corresponding $\Delta T$ value will be added to the first pacing period T and subtracted from the second pacing period T. This is more clearly illustrated in FIG. 4, which shows three pacing pulses P1, P2 and P3 in two pacing periods with the combined duration 2T. The first pulse P1 occurs at the time t1 and the last pulse P3 at the time t3, whereas the middle pulse P2 is displaced to the left of the time t2, indicating a parameter value within the range $-\Delta T max$ in FIG. 3. Thus, the first pacing period has a duration of $T-\Delta T$ and the second has the duration $T+\Delta T$. The parameter value is established by measuring the position of the middle pulse P2 with respect to the position of the pulses P1 and P3.

The flow chart of a program for reading out the parameter values from the memory 10 is illustrated in FIG. 5. It is assumed that all parameter values are stored in consecutive memory locations, the lowest memory address having the symbolic name FIRST and the highest memory address having the symbolic name LAST. The parameter value is called K and has a value in the range from 0 to 15. The pacing period is represented in the program by the variable T, the value of which is the number of clock pulses delivered to the counter 12 from the clock 11 in one pacing period. Assuming the previously mentioned pacing rate in the magnetic mode of 100 pulses per minute, the initial value of T will be 60. The program starts by setting the memory address MA at the lowest value, and then the parameter value K is red from that memory location. Thereafter, a positive or negative value for $\Delta T$ is calculated, depending upon whether K is smaller than 8 or not. If, as an example, K=0, then $\Delta T$ will be given the value 8. This value is then subtracted from T, giving the new value T=52. The program then waits while the main program causes the counter 12 to be loaded with the new value of T and a pacing pulse has been generated. Control then returns to the program in FIG. 5 which increases T by $2\Delta T$, giving a new value T=68. The program waits again for the value T to be loaded into the counter and for a new pacing pulse to be generated, whereafter T is reset to its original value by subtracting $\Delta T$. It will be seen that, by the subtraction and addition of $\Delta T$ to the original value of T, one pacing period will be shortened to 520 ms whereas the next pacing period will be lenghtened to 680 ms, resulting in a spacing between pulses such as illustrated in FIG. 4. The next step in the program of FIG. 5 is to test whether the highest memory address has been reached. If this is not the case, MA is incremented and the program returns for reading the value K of the next parameter from the new memory address. When the highest memory address (LAST) has been reached, the program ends.

Although the pacing period T in the magnetic mode is programmed at a certain fixed value, the actual length of the period T will depend upon electrical parameters of the individual pacemaker, particularly the state of the battery. If the period T is set initially to 600 ms, the actual length of the period will typically be around 700 ms towards the end of battery life. Such variations are automatically compensated for using the method of the present invention, since a parameter value is represented by the position of pulse P2 relative to the pulses P1 and P3, regardless of the actual length of the double period 2T (FIG. 4).

The position of the pulse P2 within the interval 2T may of course by observed with the aid of ECG Equipment. It would be more convenient, however, to provide the external programming apparatus with electronic circuits for measuring the spacing between pulses and numerical or alphanumerical display means for automatically displaying the parameter values.

Although the invention has been described hereabove in connection with a microprocessor-controlled pacemaker of the general type illustrated in FIG. 1, it should be understood that the invention is applicable also to other types of pacemakers, and that other variations are conceivable within the scope of the claims.

Claims:

1. A method of determining the values of the programmable parameters of an implanted programmable pacemaker, comprising:
    operating the pacemaker in asynchronous mode with a pacing period T;
    assigning to each parameter value a time $\Delta T$ which is a fraction of the period T;
    in a pair of successive pacing intervals with the combined duration of 2T shortening one interval and lengthening the other by the amount $\Delta T$; and
    comparing the relative lengths of said intervals, thereby identifying the parameter value.

2. The method according to claim 1, wherein $\Delta T$ has a positive and a negative range of values, thereby causing the total range of $\Delta T$ values to extend to both sides of the middle of the 2T interval.

3. The method according to claim 2, wherein a maximum of sixteen programmable values per parameter are represented by eight positive and eight negative $\Delta T$ values.

* * * * *